(12) United States Patent
Schiff et al.

(10) Patent No.: US 11,717,608 B1
(45) Date of Patent: Aug. 8, 2023

(54) DRUG DELIVERY ASSEMBLY INCLUDING AN ADHESIVE PAD

(71) Applicant: Fresenius Kabi Deutschland GmbH, Bad Homburg (DE)

(72) Inventors: David R Schiff, Highland Park, NJ (US); Sharon D West, Elkins Park, PA (US); Justin Bechstein, Philadelphia, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/306,533

(22) Filed: May 3, 2021

(51) Int. Cl.
*A61M 5/142* (2006.01)
*A61M 5/14* (2006.01)

(52) U.S. Cl.
CPC ...... *A61M 5/14248* (2013.01); *A61M 5/1413* (2013.01); *A61M 2005/14268* (2013.01); *A61M 2205/273* (2013.01); *A61M 2205/3331* (2013.01)

(58) Field of Classification Search
CPC ............ A61M 5/14248; A61M 5/1413; A61M 2005/14268; A61M 2205/3331; A61M 2205/273
See application file for complete search history.

(56) References Cited

U.S. PATENT DOCUMENTS

| | | | | |
|---|---|---|---|---|
| 2002/0169439 | A1* | 11/2002 | Flaherty | A61P 9/10 604/891.1 |
| 2003/0088238 | A1* | 5/2003 | Poulsen | A61M 5/1413 604/890.1 |
| 2003/0167036 | A1 | 9/2003 | Flaherty | |
| 2004/0116866 | A1 | 6/2004 | Gorman et al. | |
| 2004/0199123 | A1 | 10/2004 | Nielsen | |
| 2008/0091139 | A1* | 4/2008 | Srinivasan | A61M 5/30 604/68 |
| 2008/0125700 | A1 | 5/2008 | Moberg et al. | |
| 2009/0131860 | A1* | 5/2009 | Nielsen | A61M 5/172 604/66 |
| 2010/0137832 | A1 | 6/2010 | Mathews et al. | |
| 2010/0262078 | A1 | 10/2010 | Blomquist | |

(Continued)

FOREIGN PATENT DOCUMENTS

| | | |
|---|---|---|
| WO | 2018081234 A1 | 5/2018 |
| WO | 2018183039 A1 | 10/2018 |

(Continued)

*Primary Examiner* — Jenna Zhang (74) *Attorney, Agent, or Firm* — Cook Alex Ltd.

(57) ABSTRACT

A drug delivery assembly is provided for delivering a medicament to a patient via a fluid flow path. The assembly includes a main body having a body housing with a body interface and a controller. The assembly also includes a cartridge having a cartridge housing with a cartridge interface configured to be removably associated to the body interface. A drug reservoir positioned within the cartridge housing is configured to contain a medicament and includes an outlet. An adhesive pad is associated with a surface of the cartridge housing and is configured to removably attach to a human body surface. The controller is configured to execute a drug delivery routine in which at least a portion of the medicament in the drug reservoir is delivered to a subject via the outlet and the fluid flow path when the main body is coupled to the cartridge.

15 Claims, 3 Drawing Sheets

(56) References Cited

U.S. PATENT DOCUMENTS

| | | |
|---|---|---|
| 2011/0178461 A1* | 7/2011 | Chong .............. A61M 5/14248 604/151 |
| 2012/0010594 A1 | 1/2012 | Holt et al. |
| 2015/0374919 A1 | 12/2015 | Gibson |
| 2016/0038689 A1 | 2/2016 | Lee et al. |
| 2016/0082182 A1 | 3/2016 | Gregory et al. |
| 2016/0199574 A1 | 7/2016 | Ring et al. |
| 2016/0220798 A1* | 8/2016 | Netzel ................... A61M 35/00 |
| 2016/0296704 A1 | 10/2016 | Gibson |
| 2016/0354555 A1 | 12/2016 | Gibson et al. |
| 2017/0119969 A1 | 5/2017 | McCullough et al. |
| 2017/0124284 A1 | 5/2017 | McCullough et al. |
| 2017/0147787 A1 | 5/2017 | Albrecht et al. |
| 2017/0182253 A1 | 6/2017 | Folk et al. |
| 2017/0340837 A1 | 11/2017 | Nazzaro et al. |
| 2017/0361015 A1 | 12/2017 | McCullough |
| 2017/0368260 A1 | 12/2017 | McCullough et al. |
| 2018/0021508 A1 | 1/2018 | Destefano et al. |
| 2018/0028747 A1 | 2/2018 | Hanson et al. |
| 2018/0036476 A1 | 2/2018 | McCullough et al. |
| 2018/0085517 A1 | 3/2018 | Laurence et al. |
| 2018/0256823 A1 | 9/2018 | Nazzaro et al. |
| 2018/0272059 A1 | 9/2018 | Marbet et al. |
| 2018/0304014 A1 | 10/2018 | Knudsen et al. |
| 2019/0009019 A1 | 1/2019 | Shor et al. |
| 2019/0022306 A1* | 1/2019 | Gibson ................. A61M 5/142 |
| 2019/0050375 A1 | 2/2019 | Fitzgibbon et al. |
| 2019/0060562 A1 | 2/2019 | Olivas et al. |
| 2019/0083702 A1 | 3/2019 | Nekouzadeh et al. |
| 2019/0134296 A1 | 5/2019 | Barbedette et al. |
| 2019/0143043 A1 | 5/2019 | Coles et al. |
| 2019/0143047 A1 | 5/2019 | Jazayeri et al. |
| 2019/0151544 A1 | 5/2019 | Stonecipher |
| 2019/0167908 A1 | 6/2019 | Fitzgibbon et al. |
| 2019/0192766 A1 | 6/2019 | Stonecipher |
| 2019/0247579 A1 | 8/2019 | Damestani et al. |
| 2019/0275241 A1 | 9/2019 | Ring et al. |
| 2019/0328965 A1 | 10/2019 | Moberg |
| 2019/0365986 A1 | 12/2019 | Coiner et al. |
| 2019/0374707 A1 | 12/2019 | Damestani et al. |
| 2019/0381238 A1 | 12/2019 | Stonecipher et al. |
| 2020/0023122 A1 | 1/2020 | McCullough et al. |
| 2020/0164145 A1 | 5/2020 | Chang et al. |
| 2020/0164155 A1 | 5/2020 | Mojarrad et al. |
| 2020/0179609 A1 | 6/2020 | Tan-Malecki et al. |
| 2020/0197628 A1 | 6/2020 | McCullough et al. |
| 2020/0206429 A1 | 7/2020 | Hering et al. |
| 2020/0230313 A1 | 7/2020 | Mojarrad et al. |
| 2020/0238004 A1 | 7/2020 | McCullough |
| 2020/0254172 A1 | 8/2020 | Forster et al. |
| 2020/0261643 A1* | 8/2020 | Boyaval ............ A61M 5/14248 |
| 2020/0261648 A1 | 8/2020 | Groszmann et al. |
| 2020/0261657 A1 | 8/2020 | Gibson et al. |
| 2020/0289745 A1 | 9/2020 | Harris et al. |
| 2020/0297927 A1 | 9/2020 | Conrath et al. |
| 2020/0322793 A1 | 10/2020 | Yang |
| 2020/0338271 A1 | 10/2020 | Harris et al. |
| 2020/0345929 A1* | 11/2020 | Ben-David ....... A61M 5/14248 |
| 2021/0228799 A1* | 7/2021 | Streit ................ A61M 5/14248 |
| 2022/0339348 A1* | 10/2022 | Othel-Jacobsen .... A61M 5/322 |

FOREIGN PATENT DOCUMENTS

| | | |
|---|---|---|
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

* cited by examiner

DRUG DELIVERY ASSEMBLY INCLUDING AN ADHESIVE PAD

BACKGROUND

Field of the Disclosure

The present disclosure relates to drug delivery devices. More particularly, the present disclosure relates to devices mounted to the body for automatically delivering a drug to a patient.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

Figure 1:
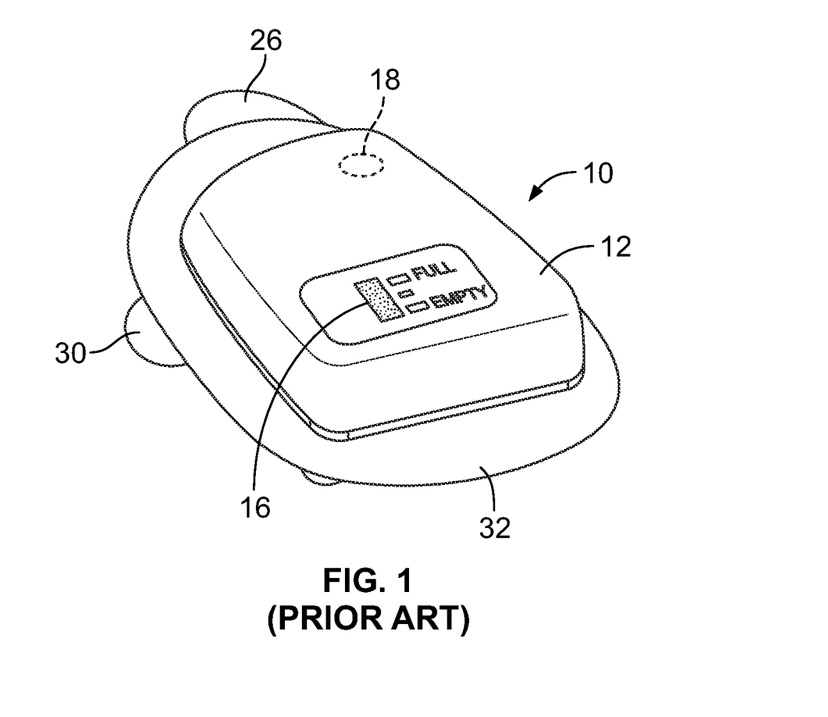
FIG. 1 is a top perspective view of a drug delivery device according to conventional design.
Figure 2:
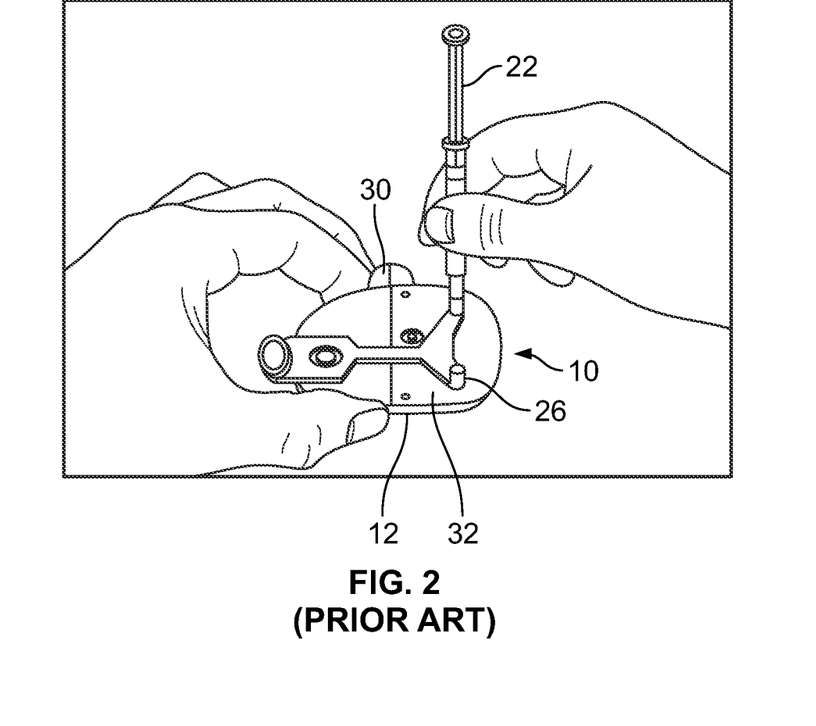
FIG. 2 is a bottom perspective view of the drug delivery device of FIG. 1.
Figure 3:
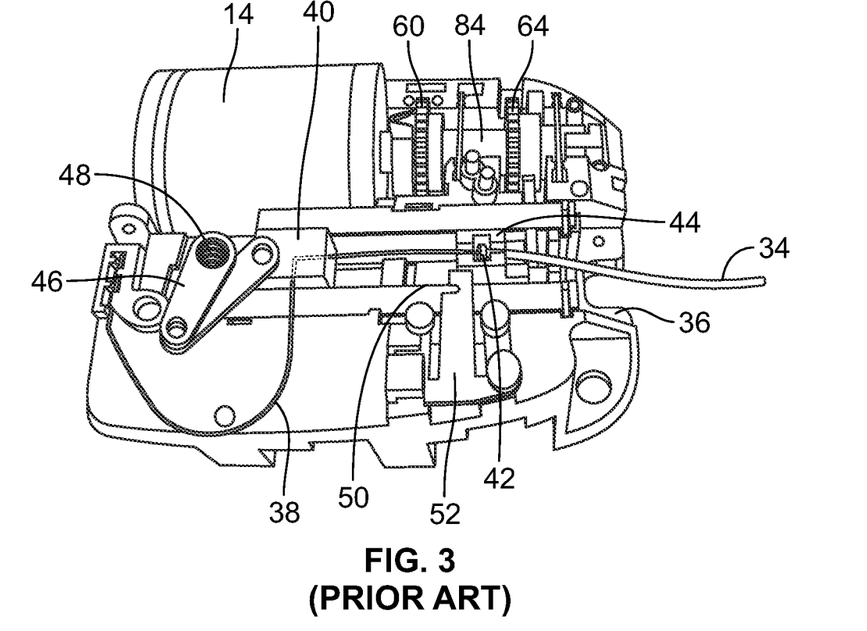
FIG. 3 is a top perspective view of the interior components of the drug delivery device of FIG. 1.
Figure 4:
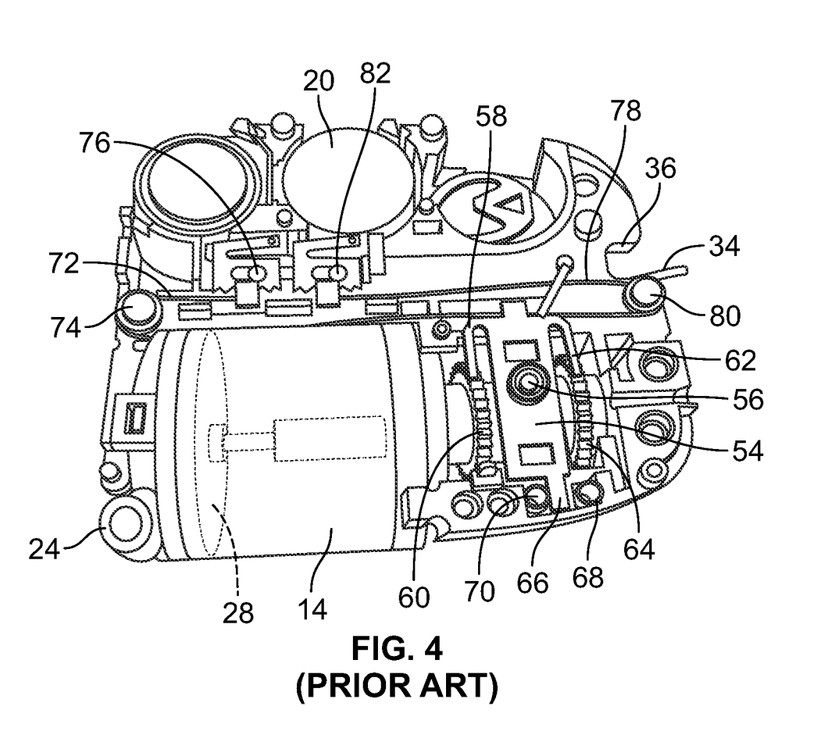
FIG. 4 is a bottom perspective view of the interior components of the drug delivery device of FIG. 1.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, such devices integrate the drug reservoir into the housing of the device, which makes the device a single-use article that must be disposed of after use. Thus, it would be advantageous to provide a device configured to allow refill and reuse, rather than requiring removal and replacement of the entire device after every use.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a drug delivery assembly defining a fluid flow path is disclosed. The assembly includes a main body and a cartridge. The main body has a body housing including a body interface and a controller. The cartridge includes a cartridge housing having a cartridge interface configured to be removably associated to the body interface. The cartridge further includes a drug reservoir positioned within the cartridge housing. The drug reservoir includes an outlet and is configured to contain a medicament. The controller is configured to execute a drug delivery routine in which at least a portion of the medicament in the drug reservoir is delivered to a subject via the outlet and the fluid flow path. Additionally, the cartridge has an adhesive pad associated with a surface of the cartridge housing and configured to removably attach to a human body surface.

In a second aspect, a drug delivery cartridge is provided for use in combination with a main body including a body housing having a body interface and a controller configured to execute a drug delivery routine in which a medicament is delivered to a subject via a fluid flow path. The cartridge has a cartridge housing including a cartridge interface configured to be removably associated to the body interface. The cartridge also includes a drug reservoir positioned within the cartridge housing. The drug reservoir has an outlet and is configured to contain a medicament. Additionally, an adhesive pad is associated with a surface of the cartridge housing and is configured to removably attach to a human body surface.

In yet another aspect, a main body is provided for use in combination with a drug delivery cartridge including: a cartridge housing having a cartridge interface; a drug reservoir, including an outlet and configured to contain a medicament, positioned within the cartridge housing; and an adhesive pad associated with a surface of the cartridge housing and configured to removably attach to a human body surface. The main body includes a body housing having a body interface configured to removably attach to the cartridge interface. The main body also includes a controller configured to execute a drug delivery routine in which at least a portion of the medicament in the drug reservoir is delivered to a subject via the outlet and a fluid flow path. Notably, the main body does not include an adhesive pad configured to attach to a human body surface.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 5:
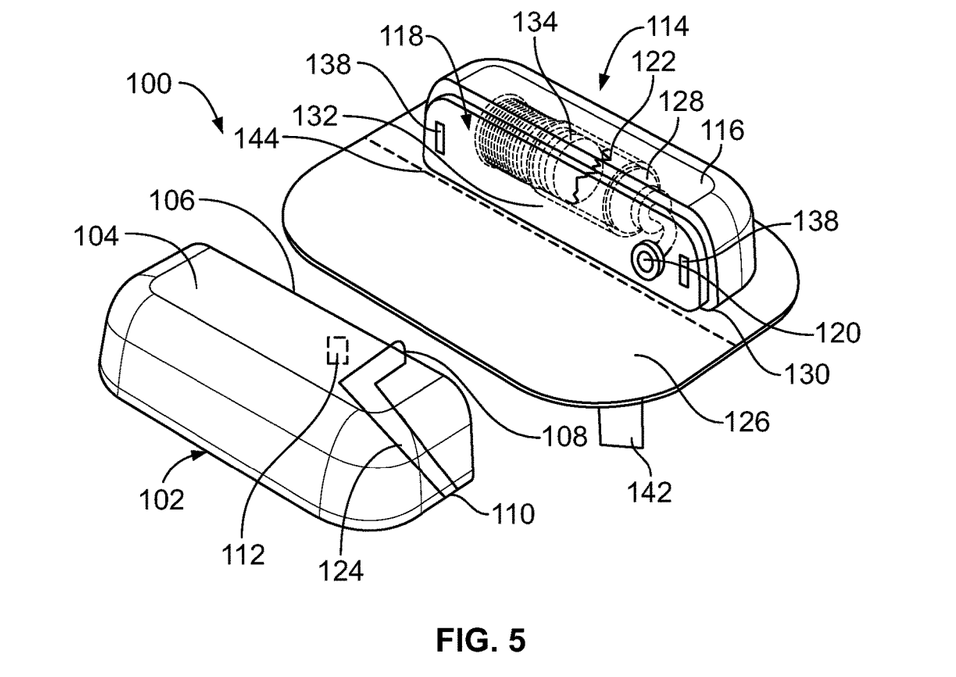
FIG. 5 is a top perspective view of an exemplary embodiment of a drug delivery assembly according to an aspect of the present disclosure, showing a cartridge of the assembly separated from a main body of the assembly.
Figure 6:
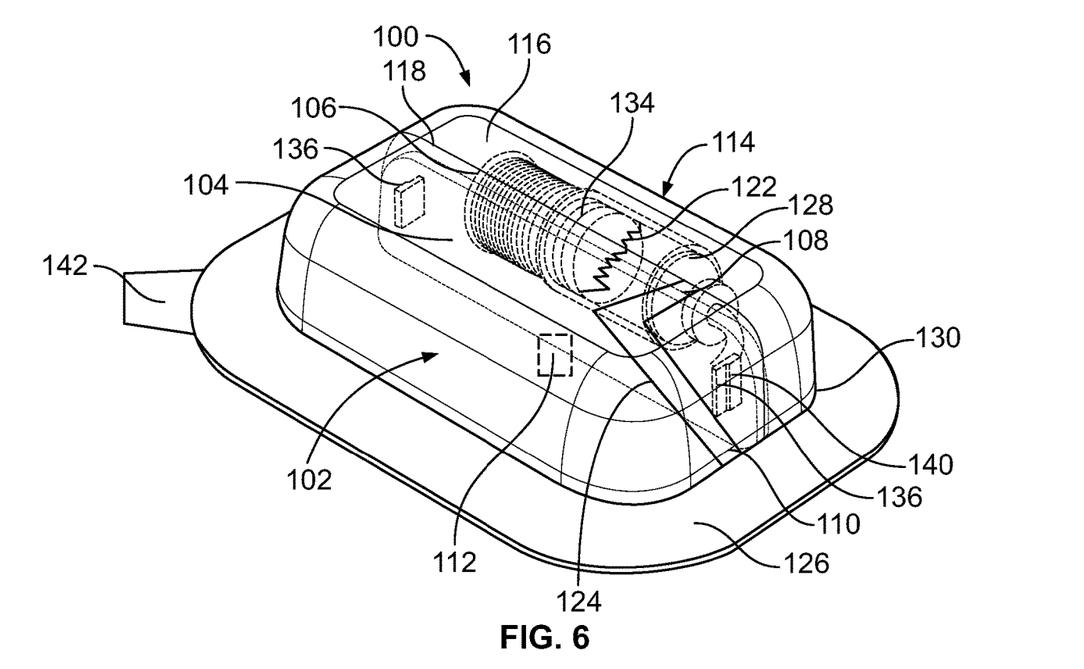
FIG. 6 is a top perspective view of the drug delivery assembly of FIG. 5, showing the cartridge associated with the main body.

FIGS. 5 and 6 show an exemplary embodiment of a drug delivery assembly 100 according to the present disclosure. The drug delivery assembly 100 includes a main body 102 and a cartridge 114 that are provided separately (FIG. 5) prior to execution of a drug delivery routine. In preparation for a drug delivery routine to be executed, the main body 102 and cartridge 114 are associated or coupled together (FIG. 6), with an adhesive pad 126 of the cartridge 114 being used to removably secure the assembled drug delivery assembly 100 to a human body surface. By such a configuration, drug delivery assemblies according to the present disclosure allow for reuse of the main body 102 for subsequent doses, rather than requiring the entire assembly to be disposed of.

Turning first to the main body 102, it includes a body housing 104 having a body interface 106. The body housing 104 may be made from any suitable, generally rigid material, including plastic polymers such as polyvinyl chloride (PVC), polypropylene, polycarbonate, and polystyrene. The body housing 104 may include at least one body latch 136 (shown in FIG. 6), which may be associated with the body interface 106.

In the illustrated embodiment, a fluid flow path 124 extends through the body housing 104 between first and second ends 108 and 110. The fluid flow path 124 may be variously configured without departing from the scope of the present disclosure, including having one or more portions that are defined by an interior surface of the body housing 104, one or more potions that are defined by an exterior surface of the body housing 104, and/or one or more portions that are defined by components associated with or incorporated into the body housing 104. The first end 108 of the fluid flow path 124 may be associated with the body interface 106, while the second end 110 may be associated with or positioned adjacent to the body housing 104 and configured to enter a human body. In an exemplary embodiment, the second end 110 of the fluid flow path 124 is configured as a needle and/or a cannula (e.g., of the type described above with regard to the device 10 of FIGS. 1-4) configured to penetrate a human body surface, such that the fluid flow path 124 may form a fluid connection between the first end 108 and a human body to which the drug delivery assembly 100 is secured. While FIGS. 5 and 6 show the fluid flow path 124 defined entirely by the main body 102, it is also within the scope of this disclosure for the flow path to instead be defined by the cartridge 114 only or for the flow path to be partially defined by the main body 102 and also partially defined by the cartridge 114.

The main body 102 also includes a controller 112 coupled to a power source (e.g., a battery). The controller 112 is configured to command the various electrical components of the drug delivery assembly 100 to execute a drug delivery routine, which may include any of a number of possible steps, including actuating the flow of fluid, such that the fluid will flow through the flow path 124 (as will be described below in further detail). The controller 112 may be variously configured without departing from the scope of the present disclosure, with the controller 112 being provided in an exemplary embodiment as a CPU or MPU configured as a computer chip mounted to a printed circuit board positioned within the body housing 104 that carries programmable software for executing the drug delivery routine.

As for the cartridge 114, it includes a cartridge housing 116 (formed of any suitable, generally rigid material, such as a PVC or other plastic material) having a cartridge interface 118 configured to be removably associated to the body interface 106. The cartridge interface 118 may include at least a portion of a side surface 132 of the cartridge housing 116. In the embodiment shown, the cartridge interface 118 protrudes from the cartridge housing 116 and the body interface 106 is recessed, so as to mate with the cartridge interface 118 upon association (the mated configuration is shown in FIG. 6). The cartridge housing 116 may also include at least one cartridge latch 138 (illustrated in FIG. 5 as a pair of latches 138) configured to detachably or permanently associate with the corresponding body latch 136 (illustrated in FIG. 6 as a pair of latches 136) when the cartridge interface 118 is associated to the body interface 106. The cartridge 114 and main body 102 are to remain in association during a drug delivery routine, so it may be advantageous to provide the assembly 100 with a lock 140 (as shown in FIG. 6) configured to associate with the body latch 136 and/or the cartridge latch 138. The controller 112 may be configured to actuate the lock 140 to prevent disengagement of the body latch 136 and the cartridge latch 138 during the drug delivery routine. The controller 112 may also be configured to actuate the lock 140 to allow disengagement of the body latch 136 and the cartridge latch 138 after the end of the drug delivery routine.

A suitable latch and locking system is described in U.S. patent application Ser. No. 17/180,594, which is hereby incorporated herein by reference. Though such a latch and locking system is suitable (and illustrated in FIGS. 5 and 6), in alternative embodiments other configurations may be used for associating the cartridge interface with the body interface.

A drug reservoir 128 is positioned within the cartridge housing 116. The drug reservoir 128 includes an outlet 120 (shown in FIG. 5) and contains a medicament 122. When the cartridge interface 118 is associated with the body interface 106, the outlet 120 is configured to fluidically connect to the first end 108 of the fluid flow path 124 of the main body 102. The drug reservoir 128 may be made from any suitable material, which may include generally rigid materials (e.g., polyethylene terephthalate) and generally flexible materials (e.g., a PVC film). On account of the medicament 122 being stored in the cartridge 114, it will be seen that drug delivery assemblies according to the present disclosure facilitate separate storage of the medicament 122 and the main body 102. Accordingly, when a medicament 122 may need to be refrigerated or frozen, the main body 102 may still remain at room temperature, as it is stored separately.

In all embodiments described herein, the medicament 122 may be any suitable fluid medication. In an exemplary embodiment, the medicament may be pegfilgrastim, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

In an exemplary embodiment, a seal may be associated with the outlet 120 (e.g., associated with the cartridge interface 118), preventing the medicament 122 from exiting the drug reservoir 128 via the outlet 120. In such an embodiment, the first end 108 of the fluid flow path 124 may be configured such that, when the cartridge interface 118 is at least partially received by the main body interface 106, the first end 108 of the fluid flow path 124 will engage or contact and open the seal so as to place the fluid flow path 124 into fluid communication with the outlet 120 of the drug reservoir 128. Accordingly, the first end 108 of the fluid flow path 124 may be configured as a projection (e.g., a generally cylindrical or tubular formation) extending from the main body interface 106 that is at least partially received by the outlet 120 to pierce the seal. The seal may be a frangible seal formed of a thin film or foil material, for example.

After the drug reservoir 128 is fluidically connected to the fluid flow path 124, the controller 112 is configured to execute a drug delivery routine in which at least a portion of the medicament 122 in the drug reservoir 128 is delivered to a subject via the fluid flow path 124. For example, the fluidic connection may trigger a mechanical or electronic signal to the controller 112 which communicates that it is time to execute the drug delivery routine. In an exemplary embodiment, a piston 134 is movably associated with the drug reservoir 128. Upon initiation of the drug delivery routine, the controller 112 may communicate with the piston 134 (for example by a suitable electronic or mechanical mechanism) such that the piston 134 pushes the medicament 122 out of the drug reservoir 128 to the first end 108 of the flow path 124, and ultimately out of the second end 110 of the flow path 124, delivering the medicament 122 to the subject.

As noted above, an adhesive pad 126 (typically comprising a substrate and associated adhesive) is associated with or affixed to the cartridge housing 116, with the adhesive pad 126 being configured to removably attach to a human body surface. In the embodiment shown in FIGS. 5 and 6, the substrate of the adhesive pad 126 is attached to a lower surface 130 of the cartridge housing 116, with the adhesive facing away from the cartridge housing 116. In alternative embodiments the adhesive pad 126 may be associated with any appropriate surface of the cartridge housing 116 (for example, a side surface of the housing that is left exposed when the cartridge 114 is associated with the main body 102). Any suitable substrate and medical grade adhesive pad configured to be removably attached to a human body surface may be used. Typically, the substrate is made of non-woven, fibrous material, such as polyethylene, PVC, polyurethane, polyethylene terephthalate, polypropylene, viscose/rayon, thermoplastic elastomer and the like. Examples of suitable adhesives useful with such substrates include any medical-grade or skin contact adhesives such as, but not limited to, acrylic or acrylate compositions, synthetic rubber, hydrocolloid, silicone and the like.

In the embodiment shown in FIGS. 5 and 6, the adhesive pad 126 is sized and configured to accommodate the entire main body 102 when the main body 102 is associated with or coupled to the cartridge 114. In embodiments in which the adhesive pad 126 is configured to accommodate the entire main body 102, an upper surface of the adhesive pad 126 (i.e., the surface of the substrate opposite the surface to which the adhesive is applied) may include a formation or material configured to an adjacent surface of the main body 102. For example, the upper surface of the adhesive pad 126 may be provided with a seat configured to receive a portion of the main body 102 or a second adhesive to temporarily retain the main body 102 in position with regard to the adhesive pad 126. While it is within the scope of the present disclosure for the main body 102 to contact some portion of the adhesive pad 126, it should also be understood that the main body 102 may instead be configured to be entirely spaced away from the adhesive pad 126 when the main body 102 is coupled to the cartridge 114.

In alternative embodiments, the adhesive pad may be sized and configured to accommodate less than the entire main body (i.e., with a portion of the perimeter of the main body extending outwardly of the perimeter of the adhesive pad). This may include the adhesive pad being manufactured with a relatively small surface area or a larger adhesive pad being altered, such as by cutting or otherwise removing a portion of it, to reduce the size. For example, as shown in FIG. 5, the adhesive pad 126 may include a perforation 144 such that a user may cut along the perforation 144 to alter the size of the adhesive pad 126, so that the perimeter of the adhesive pad 126 would accommodate only a portion of the main body 102. This may be advantageous in order to tailor the surface area of the adhesive pad to the human body surface to which it is to be removably attached. For instance, when a medicament dose is to be administered to a young child, there is a reduced human body surface area (relative to an adult) onto which the adhesive pad can attach. In this instance, a medical professional may use an embodiment having an adhesive pad that is smaller in surface area and accommodates only a portion of the main body, so that the adhesive pad may more easily fit onto the smaller human body surface. As is the case with larger adhesive pads, it should be understood that a relatively small adhesive pad may be configured to either contact an associated main body 102 or be spaced away from the main body 102 when the main body 102 is coupled to the cartridge 114.

In addition to the possibility of the perimeter of the adhesive pad being variously sized and shaped, the remainder of the adhesive pad may also be variously configured without departing from the scope of the present disclosure. For example, in one embodiment the adhesive pad may include a space or opening configured to accommodate the needle and/or cannula of the cartridge. In such an embodiment, the needle and/or cannula may pass through the space defined by the adhesive pad and enter the human body surface without having to pierce through the pad itself. In such an embodiment, the needle and/or cannula may be protected by a seal that covers the second end of the fluid flow path, until the needle and/or cannula pierces the human body surface.

In any event, after completion of the drug delivery procedure, a user may detach the cartridge 114 from the main body 102 and dispose of the cartridge 114. To dispose of the cartridge 114 the user removes the adhesive pad 126 from the user's body surface. In an exemplary embodiment, the adhesive pad 126 may include a pull tab 142 or other pullable member which facilitates removal of the adhesive pad 126 and the associated cartridge 114. In this configuration, the cartridge 114 and the associated adhesive pad 126 are a single-use item. After the main body 102 is detached from the cartridge 114, following the drug delivery routine, the cartridge 114 is disposed of and the main body 102 is put aside for future use. When the user needs a subsequent dose of the medicament 122, a new cartridge 114 is attached to the human body surface of the user via the adhesive pad 126. After attachment of the cartridge 114 to the human body surface, the main body 102 is removably associated with the cartridge 114 to facilitate execution of the drug delivery routine. Alternatively, the main body 102 may be coupled to the cartridge 114 before securing the drug delivery assembly 100 to the patient.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A drug delivery assembly defining a fluid flow path, comprising:
   a main body including
      a body housing having a body interface, and
      a controller; and
   a cartridge including
      a cartridge housing having a cartridge interface configured to be removably associated to the body interface,
      a drug reservoir positioned within the cartridge housing, the drug reservoir including an outlet and configured to contain a medicament, and
      a substantially planar adhesive pad having an upper surface secured to a surface of the cartridge housing and a lower surface configured to removably attach to a human body surface, the upper surface of the adhesive pad including a portion configured to accommodate a portion of a bottom surface of the main body and having an adhesive configured to directly contact said portion of the bottom surface of the main body to temporarily retain the main body in position with regard to the adhesive pad,
   wherein
      the fluid flow path extends from the outlet of the drug reservoir, through a first portion extending through the cartridge housing, through a second portion extending through the body housing, and to an outlet of the second portion,
      the controller is configured to execute a drug delivery routine in which at least a portion of the medicament in the drug reservoir is delivered to a subject via the outlet and the fluid flow path, and
      the body interface and the cartridge interface are oriented substantially perpendicularly with respect to a plane in which the adhesive pad extends.

2. The drug delivery assembly of claim 1, wherein the adhesive pad is configured to accommodate at least another portion of the main body.

3. The drug delivery assembly of claim 1, wherein the adhesive pad is configured to accommodate the entire main body.

4. The drug delivery assembly of claim 1, wherein the cartridge is configured as a single-use item.

5. The drug delivery assembly of claim 1, wherein the adhesive pad is attached to a lower surface of the cartridge housing.

6. The drug delivery assembly of claim 1, wherein the adhesive pad includes a perforation configured to allow for a first portion of the adhesive pad to be removed from a second portion of the adhesive pad.

7. A drug delivery cartridge for use in combination with a main body including a body housing having a body interface and a controller configured to execute a drug delivery routine in which a medicament is delivered to a subject via a fluid flow path having a second portion extending through the body housing to an outlet of the second portion, the drug delivery cartridge comprising:
   a cartridge housing including a cartridge interface configured to be removably associated to the body interface;
   a drug reservoir positioned within the cartridge housing, the drug reservoir including an outlet and configured to contain a medicament; and a substantially planar adhesive pad having an upper surface secured to a surface of the cartridge housing and a lower surface configured to removably attach to a human body surface, the upper surface of the adhesive pad including a portion configured to accommodate a portion of a bottom surface of the main body and having an adhesive configured to directly contact said portion of the bottom surface of the main body to temporarily retain the main body in position with regard to the adhesive pad, wherein
the fluid flow path extends from the outlet of the drug reservoir, through a first portion of the fluid flow path extending through the cartridge housing, and to the second portion of the fluid flow path when the cartridge interface is associated to the body interface, and
the cartridge interface is oriented substantially perpendicularly with respect to a plane in which the adhesive pad extends.

8. The drug delivery cartridge of claim 7, wherein the adhesive pad is configured to accommodate at least another portion of the main body.

9. The drug delivery cartridge of claim 7, where the adhesive pad is configured to accommodate the entire main body.

10. The drug delivery cartridge of claim 7, configured as a single-use item.

11. The drug delivery cartridge of claim 7, wherein the adhesive pad is attached to a lower surface of the cartridge.

12. The drug delivery cartridge of claim 7, wherein the adhesive pad includes a perforation configured to allow for a first portion of the adhesive pad to be removed from a second portion of the adhesive pad.

13. A main body for use in combination with a drug delivery cartridge including a cartridge housing having a cartridge interface, a drug reservoir positioned within the cartridge housing, the drug reservoir including an outlet and configured to contain a medicament, and an adhesive pad extending in a plane substantially perpendicular to the cartridge interface and having an upper surface secured to a surface of the cartridge housing and a lower surface configured to removably attach to a human body surface, the main body comprising:
a body housing including a portion configured to be accommodated by a portion of the upper surface of the adhesive pad and to directly contact an adhesive associated with said portion of the upper surface of the adhesive pad to temporarily retain the main body in position with regard to the adhesive pad, the body housing having a body interface configured to removably attach to the cartridge interface; and
a controller configured to execute a drug delivery routine in which at least a portion of the medicament in the drug reservoir is delivered to a subject via a fluid flow path extending from the outlet of the drug reservoir, through a first portion of the fluid flow path extending through the cartridge housing, through a second portion of the fluid flow path extending through the body housing, and to an outlet of the second portion, wherein
the main body does not include an adhesive pad configured to attach to a human body surface, and
the body interface being oriented substantially perpendicularly with respect to the plane in which the adhesive pad extends.

14. The main body of claim 13, wherein the body housing is configured to be at least partially accommodated by the adhesive pad after the main body is coupled to the adhesive pad.

15. The main body of claim 13, wherein the body housing is configured to be entirely accommodated by the adhesive pad after the main body is coupled to the adhesive pad.

* * * * *